United States Patent [19]

Fugmann et al.

[11] Patent Number: 5,059,615
[45] Date of Patent: Oct. 22, 1991

[54] ANTIMYCOTICALLY ACTIVE CYCLOPROPYL-SUBSTITUTED AZOLYLMETHYLCARBINOLS

[75] Inventors: Burkhard Fugmann, Wuelfrath; Manfred Plempel, Haan; Klaus Stroech, Solingen; Karl H. Büchel, Burscheid, all of Fed. Rep. of Germany

[73] Assignee: Bayer Aktiengesellschaft, Leverkusen, Fed. Rep. of Germany

[21] Appl. No.: 430,204

[22] Filed: Nov. 1, 1989

[30] Foreign Application Priority Data

Nov. 19, 1988 [DE] Fed. Rep. of Germany ....... 3839170

[51] Int. Cl.[5] ..................... A61K 31/41; C07D 249/08
[52] U.S. Cl. ............................... 514/383; 548/267.6; 548/267.8; 548/268.6
[58] Field of Search ............... 548/267.8, 268.6, 267.6; 514/383

[56] References Cited

U.S. PATENT DOCUMENTS 4,925,865 5/1990 Stroech et al. ................... 548/267.8

FOREIGN PATENT DOCUMENTS 106515 4/1984 European Pat. Off. ......... 548/267.8
180850 5/1986 European Pat. Off. ......... 548/267.8

Primary Examiner—Mary C. Lee
Assistant Examiner—Patricia L. Morris
Attorney, Agent, or Firm—Sprung Horn Kramer & Woods

[57] ABSTRACT

Antimycotically active 1-cyano- and 1-carboxamidocyclopropylazolylmethylcarbinols have now been found of the formula

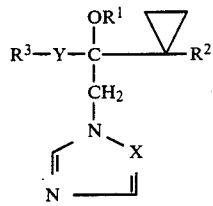

in which
$R^1$ represents hydrogen or represents alkyl or represents alkylcarbonyl,
$R^2$ represents cyano or represents a group of the formula

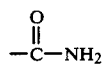

$R^3$ represents phenyl which is optionally substituted by halogen, straight-chain or branched alkyl, alkoxy, alkylthio, halogenoalkyl, halogenoalkoxy or halogenoalkylthio, or by phenyl or phenoxy which, in turn, may be substituted by halogen or alkyl having up to 6 carbon atoms,
X represents a nitrogen atom or the CH group,
Y represents a bond or represents a group of the formula

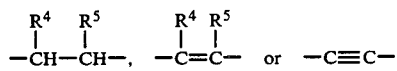

in which
$R^4$ and $R^5$ are identical or different and denote hydrogen or alkyl and their pharmaceutically tolerated acid addition salts.

9 Claims, No Drawings

ANTIMYCOTICALLY ACTIVE CYCLOPROPYL-SUBSTITUTED AZOLYLMETHYLCARBINOLS

The present invention relates to new 1-cyanocyclopropyl and 1-carboxamidocyclopropylazolylmethylcarbinol derivatives, processes for their preparation and their use in medicaments, in particular against mycoses.

It has already been disclosed that substituted azolylmethylcyclopropylcarbinol derivatives have antimycotic properties (compare EP-OS 0,180,850). However, the action of these substances is not completely satisfactory in all indication areas.

New 1-cyano- and 1-carboxamidocyclopropylazolylmethylcarbinols have now been found of the general formula (I)

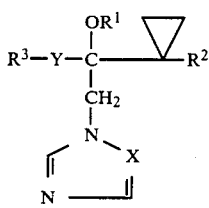
(I)

in which
R$^1$ represents hydrogen or represents alkyl having up to 10 carbon atoms or represents alkylcarbonyl having up to 8 carbon atoms,
R$^2$ represents cyano or represents a group of the formula

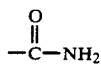

R$^3$ represents phenyl, which is optionally monosubstituted to pentasubstituted by identical or different substituents from the series comprising halogen, straight-chain or branched alkyl having up to 8 carbon atoms, alkoxy having up to 6 carbon atoms, alkylthio having up to 6 carbon atoms, halogenoalkyl, halogenoalkoxy or halogenoalkylthio having up to 6 carbon atoms in the alkyl moiety and having up to 5 halogen atoms, or by phenyl or phenoxy which, in turn, may be substituted by halogen or alkyl having up to 6 carbon atoms,
X represents a nitrogen atom or the CH group,
Y represents a bond or represents a group of the formula

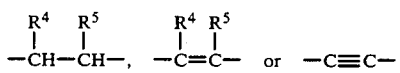

in which
R$^4$ and R$^5$ are identical or different and denote hydrogen or alkyl having up to 8 carbon atoms, and their acid addition salts.
Preferred compounds of the general formula (I) according to the invention are those in which
R$^1$ represents hydrogen or represents alkyl having up to 8 carbon atoms or represents alkylcarbonyl having up to 6 carbon atoms,
R$^2$ represents cyano or a group of the formula

represents phenyl which is optionally monosubstituted to trisubstituted by identical or different substituents from the series comprising fluorine, chlorine, bromine, straight-chain or branched alkyl having up to 6 carbon atoms, alkoxy having up to 4 carbon atoms, alkylthio having up to 4 carbon atoms, halogenoalkyl, halogenoalkoxy or halogenoalkylthio having up to 4 carbon atoms in the alkyl moiety and having up to 4 halogen atoms, or by phenyl or phenoxy which, in turn, may be substituted by fluorine, chlorine, bromine or alkyl having up to 4 carbon atoms,
X represents a nitrogen atom or the CH group,
Y represents a bond or represents a group of the formula

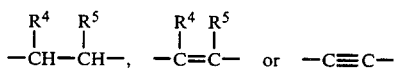

in which
R$^4$ and R$^5$ are identical or different and denote hydrogen or alkyl having up to 6 carbon atoms, and their acid addition salts.
Particularly preferred compounds of the general formula (I) according to the invention are those in which
R$^1$ represents hydrogen or represents alkyl having up to 6 carbon atoms or represents alkylcarbonyl having up to 4 carbon atoms,
R$^2$ represents cyano or the group

represents phenyl which is optionally monosubstituted or disubstituted by identical or different substituents from the series comprising fluorine, chlorine, bromine, methyl, ethyl, isopropyl, tert.-butyl, methoxy, methylthio, trifluoromethyl, trifluoromethoxy, trifluoromethylthio or by phenyl or phenoxy which, in turn, may be substituted by fluorine, chlorine, methyl or ethyl,
X represents a nitrogen atom or the CH group,
Y represents a bond or represents a group of the formula

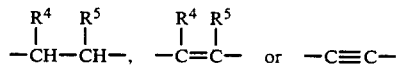

in which
R$^4$ and R$^5$ are identical or different and denote hydrogen, methyl or ethyl,
and their acid addition salts.

Preferred compounds according to the invention are also pharmacologically tolerable addition products of acids and the compounds of the general formula (I).

The acids which may be adducted preferably include hydrohalic acids, such as, for example, hydrochloric acid and hydrobromic acid, in particular hydrochloric acid, and in addition phosphoric acid, nitric acid, sulphuric acid, mono- and bifunctional carboxylic acids and hydroxycarboxylic acids, such as, for example, acetic acid, maleic acid, malonic acid, oxalic acid, gluconic acid, succinic acid, fumaric acid, tartaric acid, citric acid, salicylic acid, sorbic acid and lactic acid and also sulphonic acids, such as, for example, p-toluenesulphonic acid, 1,5-naphthalenedisulphonic acid or camphorsulphonic acid.

The compounds of the general formula (I) according to the invention and their acid addition salts show good antimicrobial, in particular good antimycotic, properties.

The substances according to the invention contain an asymmetrically substituted carbon atom. They can therefore occur in the form of optical isomers. The present invention relates both to the individual isomers and to their mixtures.

The following examples of the general formula (I) may be mentioned in addition to the compounds mentioned in the preparation examples.

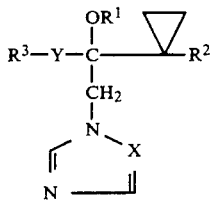

| $R^1$ | $R^2$ | $R^3$ | Y | X | M.p. |
|---|---|---|---|---|---|
| H | CN | Cl—⌬— | $CH_2$—$CH_2$ | N | 156–7° C. (A) |
| H | CN | ⌬— | CH=CH | N | (B) |
| H | CN | Cl—⌬— | CH=CH | N | (C) |
| H | CN | ⌬— | C≡C | N | 110° C. (D) |

(A) $^1$H-NMR(CDCl$_3$, δ values in ppm): 0.45b(m, 1H), 0.73(m, 1H), 1.0–1.2(m, 2H), 1.85–2.2(m, 2H), 2.7–3.0(m, 2H), 4.25(s, OH), 4.38(d, 1H), 4.55(d, 1H), 7.15(dd, 2H), 7.25(dd, 2H), 8.0(s, 1H), 8.25(s, 1H).
(D) Melting point 110° C., $^1$H-NMR(CDCl$_3$, δ values in ppm): 1.2–1.4(m, 4H), 4.6–4.75(m, 2H), 5.5(Br, s, OH), 7.25–7.4(m, 5H), 7.95(s, 1H), 8.3(s, 1H).

The compounds of the general formula (I)

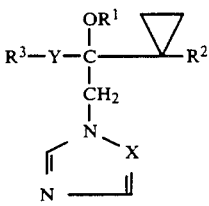

in which $R^1$, $R^2$, $R^3$, X and Y have the abovementioned meaning can be prepared stepwise by

[A] reacting compounds of the general formula (II)

in which $R^3$ and Y have the abovementioned meaning and $R^2$ represents cyano with sulphonium or sulphoxonium salts of the formula (III)

in which

Z represents halogen and
m represents a number 0 or 1 in an inert solvent, preferably dimethyl sulphoxide or in mixtures of dimethyl sulphoxide with other inert solvents, for example with tetrahydrofuran in the presence of a base, for example dimsyl sodium, sodium hydride, sodium methoxide, sodium amide or K-tert.-butoxide, at temperatures from −10° C. to 100° C. and reacting the oxiranes formed in this way of the general formula (IV)

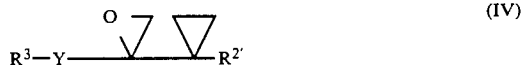

in which $R^3$ and Y have the abovementioned meaning and $R^{2'}$ represents cyano, with azoles of the formula (V)

in which

X has the abovementioned meaning and
M represents hydrogen or an alkali metal or alkaline earth metal atom, if appropriate in an inert solvent and in the presence of a base to give compounds of the formula (Ia)

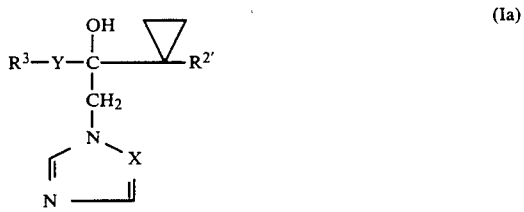

in which $R^{2'}$, $R^3$, Y and X have the abovementioned meaning, or by

[B] hydrolyzing compounds of the general formula (Ia)

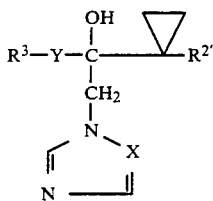

(Ia)

in which

R$^3$, X and Y have the abovementioned meaning and R$^{2'}$, represents cyano under the conditions of a phase transfer reaction in a two-phase system consisting of an aqueous solution of an alkali metal hydroxide, preferably sodium hydroxide or potassium hydroxide and an inert organic solvent, preferably benzene, toluene, chloroform or dichloromethane, with the addition of hydrogen peroxide and a catalyst, for example tetrabutylammonium chloride, benzyltriethylammonium hydroxide or tetrabutylammonium hydrogensulphonate, at temperatures from −20° C. to 60° C. partially to give compounds of the general formula (I) in which R$^{2'}$ represents the group of the formula —CO—NH$_2$, or by

[C] reacting azolylmethylcyclopropylcarbinol derivatives of the formula (I b)

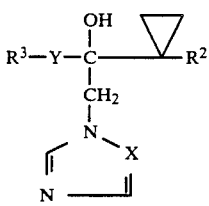

(Ib)

in which

R$^2$, R$^3$, X and Y have the abovementioned meaning, with strong bases, such as, for example, alkali metal amides or hydrides in the presence of a diluent, such as, for example, dioxane, at temperatures from 20° C. to 100° C. and reacting the alkoxides formed in this way of the general formula (I c;

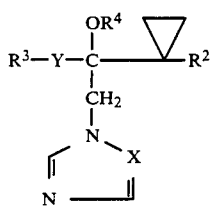

(Ic)

in which

R$^2$, R$^3$, X and Y have the abovementioned meaning and

R$^4$ represents a cationic radical of a base with compounds of the formula (VI)

 R$^5$—W (VI)

in which

R$^5$ represents alkyl having up to 10 carbon atoms, or acyl having up to 8 carbon atoms and W represents halogen in the presence of a diluent, for example dioxane, at temperatures from 20° C. to 100° C. and if appropriate subsequently adducting an acid or a metal salt in a customary manner to the compounds of the general formula (I) thus obtained.

A new process for the preparation of the compounds of the general formula (II), in which R$^{2'}$, R$^3$ and Y have the abovementioned meaning, has additionally been found by reacting N-methyl-N-methoxyamides of the formula (VII)

(VII)

in which

R$^3$ and Y have the abovementioned meaning with the lithium salt of 1-cyanocyclopropane of the formula

(VIII)

in an inert solvent, such as, for example, tetrahydrofuran or diethyl ether, in a temperature range from −100° C. to +20° C.

The compounds of the formulae (VII) and (VIII) are known (S. Weinreb, Tetrahedron Lett. 22 (1981), 3815, H. W. Pinnick et al., J. Org. Chem. 45 (1980) 4506).

The compounds of the formula (III) are also known (C. Ferri, Reaktionen der organischen Chemie (Reactions of Organic Chemistry), Thieme-Verlag, 1978).

The azoles of the formula (V) required as reaction components for carrying out process [A] according to the invention are generally known compounds of organic chemistry.

The halogen compounds of the formula (VI) are known or can be prepared by methods which are known in principle.

Process [A] can be carried out both in a one-step reaction and with isolation of the individual intermediates. The reaction is carried out in a temperature range from −20° C. to 200° C., preferably at −10° C. to 100° C., at elevated or atmospheric pressure.

Suitable solvents for processes [A] and [C] are inert solvents such as, for example, N,N-dimethylformamide, N,N-dimethylacetamide, dimethyl sulphoxide, sulpholane, N-methylpyrrolid-2-one, dioxane, tetrahydrofuran, acetonitrile, methylene chloride or an aromatic hydrocarbon such as benzene, chlorobenzene, nitrobenzene, toluene or xylene. Mixtures of the solvents mentioned by way of example may also be used.

Suitable bases for process [A] are, for example, carbonates, hydrogencarbonates, hydroxides, alkoxides or hydrides of alkali metals or alkaline earth metals such as, for example, sodium carbonate, sodium hydrogencarbonate, potassium carbonate, sodium hydroxide, sodium methoxide or sodium hydride, or organic bases, for example tertiary amines such as triethylamine, tributylamine, ethylmorpholine or pyridine, dimethylaminopyridine, quinoline or 1,5-diazabicyclo-[5,4,0]-undec-5-ene (DBU).

The bases are employed in processes [A] and [C] in equimolar amounts or a 2–3-fold molar excess relative to the other reaction components. The use of a 2-fold molar excess is preferred.

Suitable solvents for process [B] are aromatic hydrocarbons such as benzene or toluene, or aliphatic, chlorinated hydrocarbons such as, for example, dichloromethane or chloroform.

Hydroxides, hydrides or alkoxides of alkali metals or alkaline earth metals, such as, for example, sodium hydroxide, potassium hydroxide, sodium hydride, sodium methoxide or sodium ethoxide can be employed as bases.

The bases are employed in a 1–3-fold molar excess, relative to the other reaction components.

The azolylmethylcyclopropyl derivatives of the formula (Ib) required as starting substances for process [C] according to the invention are compounds according to the invention. Their conversion into the corresponding alkoxides is carried out in a generally known manner by reacting them at room temperature with suitable strong bases, such as alkali metal amides or hydrides, quaternary ammonium hydroxides or phosphonium hydroxides in an inert solvent, such as, for example, dioxane. Accordingly, $R^4$ in the compounds of the formula (Ic) preferably represents an alkali metal cation, such as a sodium or potassium cation, or a quaternary ammonium or phosphonium cation.

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtering off, and if desired, can be purified by washing with an inert organic solvent.

The compounds of the formula (I) according to the invention and their acid addition salts have antimicrobial, in particular strong antimycotic actions. They possess a very wide spectrum of antimycotic action, in particular against dermatophytes and Blastomycetes and also biphasic fungi, for example against Candida species, such as Candida albicans, Epidermophyton species, such as Epidermophyton floccosum, Aspergillus species, such as Aspergillus niger and Aspergillus fumigatus, Trichophoton species, such as Trichophyton mentagrophytes, Microsporon species, such as Microsporon felineum and also Torulopsis species, such as Torulopsis glabrata. The enumeration of these microorganisms in no case represents a limitation on the combatible microorganisms, but is only of illustrative character.

Examples of indications which may be mentioned, for example, in human medicine are:

Dermatomycoses and systemic mycoses caused by Trichophyton mentagrophytes and other Trichophyton species, Microsporon species and also Epidermophyton floccosum, Blastomycetes and biphasic fungi and also Hyphomycetes.

Areas of indication which may be mentioned, for example, in veterinary medicine are:

All dermatomycoses and systemic mycoses, in particular those which are caused by the abovementioned pathogens.

The present invention includes pharmaceutical preparations which contain one or more active compounds according to the invention or consist of one or more active compounds according to the invention in addition to nontoxic, inert pharmaceutically suitable excipients.

The present invention also includes pharmaceutical preparations in dosage units. This means that the preparations are present in the form of individual parts, for example tablets, coated tablets, capsules, pills, suppositories and ampoules, the active compound content of which corresponds to a fraction or a multiple of an individual dose. The dose units may contain, for example, 1, 2, 3 or 4 individual doses or ½, ⅓ or ¼ of an individual dose. An individual dose preferably contains the amount of active compound which is administered in one administration and which usually corresponds to a whole, a half, a third or a quarter of a daily dose.

Non-toxic, inert pharmaceutically suitable excipients are taken to mean solid, semi-solid or liquid diluents, fillers or formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders or sprays.

Tablets, coated tablets, capsules, pills and granules may contain the customary excipients, such as (a) fillers and extenders, for example starches, lactose, sucrose, glucose, mannitol and silica, (b) binders, for example carboxymethylcellulose, alginates, gelatine, polyvinylpyrrolidone, (c) humectants, for example glycerol, (d) disintegrants, for example agar-agar, calcium carbonate and sodium bicarbonate, (e) solution retardants, for example paraffin and (f) absorption accelerators, for example quaternary ammonium compounds, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i) in addition to the active compound or compounds.

The tablets, coated tablets, capsules, pills and granules may be provided with the customary coatings and coverings optionally containing opacifying agents and may be composed so that they deliver the active compound or compounds only or preferably to a certain part of the intestinal tract, optionally in a sustained manner, it being possible to use, for example, polymeric substances and waxes as embedding materials.

The active compound or compounds may optionally also be present in microencapsulated form with one or more of the abovementioned excipients.

Suppositories may contain the customary water-soluble or water-insoluble excipients, for example polyethylene glycols, fats, for example cocoa fat and higher esters (for example $C_{14}$ alcohol with $C_{16}$ fatty acid) or mixtures of these substances in addition to the active compound or compounds.

Ointments, pastes, creams and gels may contain the customary excipients, for example animal and vegetable fats, waxes, paraffins, starch, tragacanth, cellulose derivatives, polyethylene glycols, silicones, bentonites, silica, talc and zinc oxide or mixtures of these substances in addition to the active compound or compounds.

Powders and sprays may contain the customary excipients, for example lactose, talc, silica, hydrated alumina, calcium silicate and polyamide powder or mixtures of these substances, and sprays may additionally contain the customary propellants, for example chlorofluorohydrocarbons, in addition to the active compound or compounds.

Solutions and emulsions may contain the customary excipients, such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerol formal, tetrahydrofurfuryl alcohol, polyethylene glycols and fatty acid esters of sorbitan or mixtures of these substances in addition to the active compound or compounds.

For parenteral administration, the solutions and emulsions may also be present in sterile and blood-isotonic form.

Suspensions may contain the customary excipients, such as liquid diluents, for example water, ethyl alcohol, propyl alcohol, suspending agents, for example ethoxylated isostearyl alcohols, polyoxyethylene sorbitol and sorbitan esters, microcrystalline cellulose, aluminum metahydroxide, bentonite, agar-agar and tragacanth or mixtures of these substances in addition to the active compound or compounds.

The formulation forms mentioned may also contain colorants, preservatives and odor-enhancing and flavor-enhancing additives, for example peppermint oil and eucalyptus oil, and sweeteners, for example saccharin.

The therapeutically active compounds should be present in the abovementioned pharmaceutical preparations in a concentration from about 0.1 to 99.5, preferably from 0.5 to 95% by weight of the total mixture.

The abovementioned pharmaceutical preparations may also contain other pharmaceutical active compounds in addition to the active compounds according to the invention.

The abovementioned pharmaceutical preparations are prepared in a customary manner by known methods, for example by mixing the active compound or compounds with the excipient or excipients.

The present invention also includes the use of the active compounds according to the invention and pharmaceutical preparations which contain one or more active compounds according to the invention, in human and veterinary medicine for the prevention, amelioration and/or healing of the abovementioned disorders.

The active compounds or the pharmaceutical preparations may be administered locally, orally, parenterally, intraperitoneally and/or rectally, preferably orally or locally.

In general, it has proved advantageous in human and in veterinary medicine to administer the active compound or compounds according to the invention in total amounts from about 0.1 to about 200, preferably 1 to 50 mg/kg of body weight every 24 hours, if desired in the form of a number of individual doses to attain the desired results.

On oral administration, the active compounds according to the invention are administered in total amounts from about 1 to about 200, preferably 2 to 100 mg/kg of body weight every 24 hours, and on parenteral administration in total amounts of about 2.5 to about 50, preferably 1 to 25 mg/kg of body weight every 24 hours.

However, it may be necessary to deviate from the dosages mentioned, depending on the species and the body weight of the subject to be treated, the nature and severity of the disorder, the type of the preparation and the administration of the medicament and also the time period or interval within which administration takes place. Thus, in some cases it may be sufficient to manage with less than the abovementioned amount of active compound, whereas in other cases the abovementioned amount of active compound must be exceeded. The optimum dosage required in each case and the type of administration of the active compound can easily be established by any person skilled in the art on the basis of his expert knowledge.

PREPARATION EXAMPLES

EXAMPLE 1

1-(1-Cyanocyclopropyl)-1-phenyl-2-(1,2,4-triazol-1-yl)ethanol

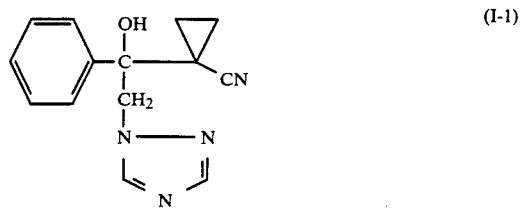

(I-1)

660 mg (0.022 mol) of (80% in oil) sodium hydride are suspended in 30 ml of abs. DMSO under argon. 4.8 g (0.022 mol) of trimethylsulphoxonium iodide (EGA) are added at RT and the mixture is stirred until evolution of hydrogen has ended. 3.4 g (20 mmol) of 1-benzoyl-1-cyanocyclopropane in 10 ml of abs. DMSO are then added rapidly. The mixture is stirred for 2 h at 40° C. and 2 g (30 mmol) of sublimed 1,2,4-triazole and 908 mg (10 mmol) of 1,2,4-triazole-Na salt (EGA) are then added. The mixture is stirred for 2 h at 50° C. and for 4 h at 80° C., cooled, stirred into ice-water and extracted with chloroform. The organic phase is washed with 2N NaOH, dried ($Na_2SO_4$) and concentrated. The residue is chromatographed on silica gel using ethyl acetate and the product is recrystallized from dichloromethane/petroleum ether. 2 g (40% of theory) of 1-(1-cyanocyclopropyl)-1-phenyl-2-(1,2,4-triazol-1-yl)ethanol having a melting point of 103°–105° C. are obtained as colorless crystals, $^1$H—NMR ($CDCl_3$):

$\delta$=0.9–1.1 (m,4H), 4.7 (d,1H), 4.9 (d,1H), 5.13 (s,1H), 7.3–7.5 (m,3H), 7.65 (m,2H), 7.95 (s,1H), 8.25 (s,1H) ppm.

EXAMPLE 2

1-(1-Cyanocyclopropyl)-1-(4-fluorophenyl)-2-(1,2,4-triazol-1-yl)ethanol

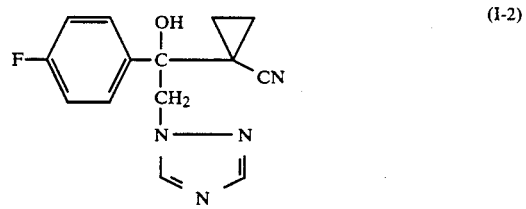

(I-2)

2.42 g (11 mmol) of trimethylsulphoxonium iodide (EGA) are added in portions at 20° C. to a suspension of 0.33 g (11 mmol) of sodium hydride (80% in oil) in 20 ml of DMSO p.a. The mixture is stirred until evolution of hydrogen has ended and 2 g (10mmol) of (4-fluoro)-1-benzoyl-1-cyanocyclopropane, dissolved in 5 ml of abs. DMSO, are rapidly added dropwise. The mixture is stirred for 1 h at RT and for 1 h at 40° C., then 1.04 g (15 mmol) of 1,2,4-triazole (sublimed) and 0.46 g (5 mmol) of 1,2,4-triazole Na salt in DMSO are added. The mixture is stirred for 2 h at 50° C. and for 4 h at 80° C., poured into ice-water and extracted using dichloromethane. The organic phase is washed with 2N sodium hydroxide solution, dried over Na$_2$SO$_4$ and concentrated. The residue is chromatographed on silica gel and the product is crystallized from diethyl ether. 1.2 g (44% of theory) of colorless crystals of 1-(1-cyanocyclopropyl)-1-(4-fluorophenyl)-2-(1,2,4-triazol-1-yl)ethanol are thus obtained having a melting point of 121°-122° C., $^1$H-NMR (CDCl$_3$): δ=0.95-1.1 (m,4H), 4.7 (d,1H), 4.9 (d,1H), 5.25 (s,1H), 7.10 (t,2H), 7.65 (dd,2H), 7.9 (s,1H), 8.28 (s,1H) ppm.

EXAMPLE 3

1-(1-Cyanocyclopropyl)-1-(4-chlorophenyl)-2-(1,2,4-triazol-1-yl)ethanol

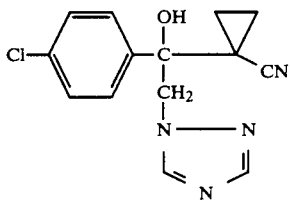
(I-3)

750 mg (0.025 mol) of sodium hydride (80% in oil) are suspended in 30 ml of abs. DMSO under argon. 5.5 g (25 mmol) of trimethylsulphoxonium iodide (EGA) are added at RT. After evolution of H$_2$ has ended, 4.6 g (25 mmol) of the ketone II-3 (Table 2) are added (in 30 ml of abs. DMSO). The mixture is stirred for 2 h at 40° C. and 2.3 g (34 mmol) of 1,2,4-triazole (EGA) and 1.03 g (11 mmol) of 1,2,4-triazole sodium salt (EGA) are then added. The mixture is stirred for 2 h at 40° C. and for 4 h at 80° C., cooled, stirred into ice-water and extracted using ethyl acetate. The organic phase is washed with 2N sodium hydroxide solution, dried using Na$_2$SO$_4$ and evaporated. The residue is chromatographed on silica gel using ethyl acetate and the product is recrystallized from dichloromethane/petroleum ether. 1.6 g (22% of theory) of 1-(1-cyanocyclopropyl)-1-(4-chlorophenyl)-2-(1,2,4-triazol-1-yl)ethanol are obtained as colorless crystals of melting point 107° C., $^1$H—NMR (CDCl$_3$):

δ=0.9-1.1 (m,4H), 4.70 (d,1H), 4.90 (d,1H), 5.24 (s,1H), 7.4 (dd,2H), 7.6 (dd,2H), 7.95 (s 1H) 8.28 (s,1H) ppm.

EXAMPLE 4

1-(1-Cyanocyclopropyl)-1-(2,4-difluorophenyl)-2-(1,2,4-triazol-1-yl)ethanol

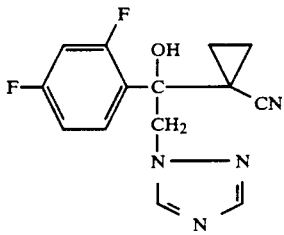
(I-4)

990mg (0.033 mol) of sodium hydride (80% in oil) are suspended in 60 ml of abs. DMSO. 7.2 g (0.033 mol) of trimethylsulphoxonium iodide (Aldrich) are added at RT. After evolution of H$_2$ has ended, 6.2g (0.03 mol) of the ketone II-12 (Table 2) in 30 ml of abs. DMSO are rapidly added. The mixture is stirred for 1 h at RT and for 1 h at 40° C., 3 g (45 mmol) of sublimed 1,2,4-triazole and 1.36 g (15 mmol) of 1,2,4-triazole sodium salt (EGA) are added, and the mixture is stirred for 2 h at 50° C. and for 5 h at 80° C. It is cooled, stirred into water and extracted using ethyl acetate. The organic phase is washed with 2N NaOH, dried over Na$_2$SO$_4$ and evaporated. The residue is chromatographed on silica gel using ethyl acetate and the product is crystallized from ethyl acetate/petroleum ether. 3.6 g (41% of theory) of 1-(1-cyanocyclopropyl)-1-(2,4-difluorophenyl)-2-(1,2,4-triazol-1-yl)ethanol are obtained as colorless crystals having a melting point of 103°-105° C., $^1$H-NMR (CDCl$_3$):

δ=1.1-1.25 (m,4H), 4.79 (d,1H), 5.28 (d,1H), 5.55 (s,1H), 6.80 (ddd,1H), 6.86 (ddd,1H), 7.60 (m,1H), 7.85 (s,1H), 8.20 (s,1H) ppm.

EXAMPLE 5

1-(1-Cyanocyclopropyl)-1-(4-fluorophenyl)-2-imidazol-1-yl)ethanol

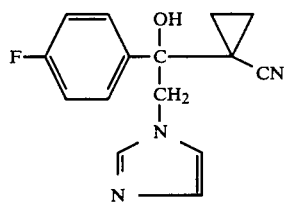
(I-5)

4 g (59 mmol) of imidazole and 2.1 g (10 mmol) of 2-(1-cyanocyclopropyl)-2-(4-fluorophenyl)oxirane (IV-2, Example 33) in 20 ml of abs. acetonitrile are heated under reflux for 8 h under a nitrogen atmosphere. After evaporation of the solvent in vacuo, the residue is taken up in ethyl acetate. The mixture is washed with water and dried over Na$_2$SO$_4$, and the solvent is evaporated in vacuo. Chromatographic purification on silica gel (eluent: dichloromethane containing 2% ethanol) gives 1.1 g (39% of theory) of 1-(1-cyanocyclopropyl)-1-(4-fluorophenyl)-2 -(imidazol-1-yl)ethanol having a melting point of 173° C. (dec.), $^1$H—NMR (CDCl$_3$):

δ=0.85-1.24 (m,4H), 4.5 (d,1H), 4.65 (d,1H), 6.68 (s,1H), 6.95 (s,1H), 7.10 (t,2H), 7.53 (s,1H), 7.65 (dd,2H) ppm.

EXAMPLE 6

2-(1-Cyanocyclopropyl)-4-phenyl-1-(1,2,4-triazol-1-yl)butan-2-ol (I-6)

0.8 g (12 mmol) of 1,2,4-triazole, 0.1 g (1 mmol) of potassium tert.-butoxide and 0.8 g (4 mmol) of 2-(1-cyanocyclopropyl)-2-(2-phenylethyl)oxirane (IV-16, Example 34) are heated to 80° C. for 6 h in 10 ml of abs. DMF. The solvent is stripped off in vacuo, and the residue is taken up in ethyl acetate and washed with water. After drying over Na₂SO₄, the solvent is evaporated in vacuo and the residue is chromatographed on silica gel (CH₂Cl₃ containing 2% ethanol). 0.3 g (28% of theory) of 2-(1-cyanocyclopropyl)-4-phenyl-1-(1,2,4-triazol- 1-yl)butan-2-ol is obtained in the form of a colorless oil, ¹H—NMR (CDCl₃):

δ=0.42-0.5 (m,1H), 0.68-0.78 (m,1H), 1.03-1.22 (m,2H), 1.93-2.05 (m,1H), 2.15 (m,1H), 2.8 (m,1H), 2.95 (m,1H), 4.27 (s,1H), 4.41 (d,1H), 4.57 (d,1H), 7.2-7.34 (m,5H), 8.02 (s,1H), 8.27 (s,1H) ppm.

EXAMPLE 7

1-(1-Carboxamidocyclopropyl)-1-(4-fluorophenyl)-2-(1,2,4-triazol-1-yl)ethanol 3.0 g (0.011 mol) of the nitrile I-2 (Example 2) are dissolved in 30 ml of chloroform. The solution is cooled to 0° C. and 10.3 ml (100 mmol) of 30% strength H₂O₂ solution, 1 g of tetrabutylammonium hydrogensulphate and 8.4 ml of 20% strength aqueous NaOH are added. During the course of 24 hours, a further 20 ml of 30% strength H₂O₂ solution are added with stirring. The mixture is diluted using dichloromethane, and the organic phase is separated off, dried using Na₂SO₄ and evaporated. The residue is crystallized from methanol and 1.9 g (60% of theory) of 1-(1-carboxamidocyclopropyl)-1-(4-fluorophenyl)-2-(1,2,4-triazol-1-yl)ethanol are obtained having a melting point of 209° C., ¹H—NMR (CDCl₃+DMSO-d₆):

δ=0.8-1.1 (m,4H), 4.65 (d,1H), 4.85 (d,1H) 6.3 (s,1H), 6.65 (br.s,1H), 6.95 (dd,2H), 7.1 (br.s,1H), 7.45 (dd,2H), 7.7 (s,1H), 8.2 (s,1H) ppm.

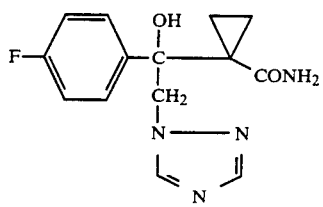

(I-7)

TABLE 1

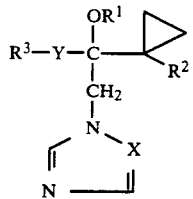

| Ex. No. | Compd. No. | R³ | R¹ | R² | X | Y | Melting point (°C.) | Spectroscopic data (¹H-NMR, CDCl₃, δ values in ppm) |
|---|---|---|---|---|---|---|---|---|
| 8 | I-8 | CH₃O—⟨phenyl⟩— | H | CN | N | — | 88-90 | 0.9-1.05(m, 4H), 3.8(s, 3H), 4.7(d, 1H), 4.9(d, 1H), 4.95 (s, 1H), 6.90(m, 2H), 7.55(m, 2H), 7.95(s, 1H), 8.23(s, 1H) |
| 9 | I-9 | CF₃O—⟨phenyl⟩— | H | CN | N | — | 57-59 | 0.9-1.1(m, 4H), 4.7(d, 1H), 4.95(d, 1H), 5.3(s, 1H), 7.25(dd, 2H), 7.70(dd, 2H), 7.95(s, 1H), 8.30(s, 1H) |
| 10 | I-10 | CF₃—⟨phenyl⟩— | H | CN | N | — | amorphous | 0.9-1.1(m, 4H), 4.7(d, 1H), 4.95(d, 1H), 5.3(s, 1H), 7.68 (d, 2H), 7.80(d, 2H), 8.0(s, 1H), 8.3(s, 1H) |
| 11 | I-11 | CF₃—⟨phenyl-Cl⟩— | H | CN | N | — | 160-162 | 1.05(m, 1H), 1.19(m, 2H), 1.35 (m, 1H), 4.8(d, 1H), 5.6(s, 1H), 5.68(d, 1H), 7.53(dd, 1H), 7.65(s, 1H), 7.93(s, 1H), 7.95(dd, 1H), 8.20(s, 1H) |
| 12 | I-12 | ⟨biphenyl⟩— | H | CN | N | — | 128-130 | 0.9-1.1(m, 4H), 4.75(d, 1H), 4.95(d, 1H), 5.2(s, 1H), 7.3-7.8(m, 9H), 7.95(s, 1H), 8.3(s, 1H) |

TABLE 1-continued $$R^3-Y-\underset{\underset{\underset{N\diagdown_X}{\overset{|}{N}}}{\overset{|}{CH_2}}}{\overset{OR^1}{\overset{|}{C}}}-\overset{\triangle}{R^2}$$

| Ex. No. | Compd. No. | R³ | R¹ | R² | X | Y | Melting point (°C.) | Spectroscopic data (¹H-NMR, CDCl₃, δ values in ppm) |
|---|---|---|---|---|---|---|---|---|
| 13 | I-13 | 2-Cl-phenyl | H | CN | N | — | 131–133 | 1.0–1.2(m, 3H), 1.35(m, 1H), 4.75(d, 1H), 5.4(s, 1H), 5.6 (d, 1H), 7.25(m, 2H), 7.35 (m, 1H), 7.75(m, 1H), 7.85 (s, 1H), 8.20(s, 1H) |
| 14 | I-14 | 2-F,4-Cl-phenyl | H | CN | N | — | 120–122 | 1.1–1.3(m, 4H), 4.75(d, 1H), 5.3(d, 1H), 5.55(s, 1H), 7.1(dd, 1H), 7.15(dd, 1H), 7.55(t, 1H), 7.85(s, 1H), 8.20(s, 1H) |
| 15 | I-15 | 2,6-diF-phenyl | H | CN | N | — | 99–101 | 1.15–1.3(m, 4H), 4.7(d, 1H), 5.4(d, 1H), 5.6(s, 1H), 6.9(dd, 2H), 7.25–7.35 (m, 1H), 7.9(s, 1H), 8.3(s, 1H) |
| 16 | I-16 | 2,4-diCl-phenyl | H | CN | N | — | 125 | 1.0–1.2(m, 3H), 1.35(m, 1H), 4.7(d, 1H), 5.5(s, 1H), 5.65 (d, 1H), 7.23(dd, 1H), 7.4 (d, 1H), 7.7(d, 1H), 7.9(s, 1H), 8.2(s, 1H) |
| 17 | I-17 | 2,4,6-triF-phenyl | H | CN | N | — | amorphous | 1.15–1.35(m, 4H), 4.65 (d, 1H), 5.35(s, 1H), 5.65 (s, 1H), 6.65(m, 2H), 7.90(s, 1H), 8.28(s, 1H) |

EXAMPLE 18

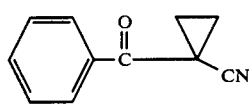

(II-1)

Process variant A 1 g (7 mmol) of α-cyanoacetophenone, 8 g (43 mmol) of 1,2-dibromoethane, 0.1 g (0.4 mmol) of 18-crown-6 and 4 g (69 mmol) of potassium fluoride are heated under reflux for 18 h as a heterogeneous system in 10 ml of dichloromethane. After cooling, the mixture is filtered, the organic phase is washed with H₂O and the solvent is evaporated in vacuo after drying over Na₂SO₄. The residue is chromatographed on a silica gel using CH₂Cl₂. 0.25 g (20% of theory) of 1-benzoyl-1-cyanocyclopropane are obtained in this manner as a colorless oil, ¹H—NMR (CDCl₃): δ=1.75 (m,2H), 1.87(m,2H), 7.5–7.7(m,3H), 8.0(dd,2H) ppm.

Process variant B 13.2 ml (0.096 mol) of diisopropylamine and 75 ml of THF p.a. are cooled to −78° C. under argon and 58.6 ml (0.096 mol) of of 1.6 M n-butyllithium in n-hexane are added dropwise. The mixture is stirred for 30 min. at −78° C., 7 ml (0.096 mol) of cyclopropylnitrile (EGA) are added and the mixture is stirred for 1 h at −78° C. 13.6 g (0.0825 mol) of N-methoxy-N-methylbenzamide (S. Weinreb, THL 1981, 3815) are added dropwise (in 50 ml of abs. THF) and the mixture is stirred for 4 h at 0° C. It is poured into ice-water and neutralized using 5% strength HCL. Ether is added. The mixture is extracted using dichloromethane, and the extract is dried with NA₂SO₄and evaporated. The residue is chromatographed on silica gel using dichloromethane and 7.1 g (50% of theory) of 1-benzoyl-1-cyanocylopropane are obtained as a colourless oil.

PRECURSORS

EXAMPLE 19

1-(4-Fluoro)benzoyl-1-cyanocyclopropane

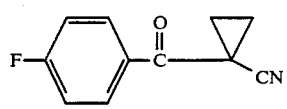

(II-2)

57.5 ml (0.41 mol) of diisopropylamine and 290 ml of abs. THF are cooled to −78° C. under argon. 255 ml (0.41 mol) of 1.6 M n-butyllithium in hexane are added dropwise and the mixture is stirred for 30 min. at −78° C. 30.1 ml (0.409 mol) of cyclopropylnitrile are slowly added dropwise and the mixture is stirred for 1 h at −78° C. 65.1 g (0.355 mol) of 4-fluoro-(N-methyl-N-methoxy)benzamide in 200 ml of abs. THF are added dropwise and the mixture is slowly allowed to come to room temperature. It is poured onto 500 ml of 5% HCl/ice-water, adjusted to neutral pH, saturated NaCl solution is added and the mixture is extracted using ethyl acetate. The extract is dired over $Na_2SO_4$ and evaporated, and the residue is crystallized from diethyl ether. 33.8 g (50.4% of theory) of colorless crystals of melting point 60°–62° C. are obtained, $^1$H—NMR (CDCl$_3$): δ = 1.75 (m,2H), 1.86 (m,2H), 7.2 (m,2H), 8.1 (m,2H) ppm.

TABLE 2

$$R^3-Y-\overset{\overset{O}{\|}}{C}-\underset{R^{2'}}{\triangleleft}$$

| Ex. No. | Compd. No. | $R^3$ | $R^{2'}$ | Y | Melting point (°C.) | Spectroscopic data, ($^1$H-NMR, CDCl$_3$, δ values in ppm) |
|---|---|---|---|---|---|---|
| 20 | II-3 | Cl—C$_6$H$_4$— | CN | bond | 68–70° C. | 1.75(m, 2H), 1.86(m, 2H), 7.5(dd, 2H), 8.0(dd, 2H) |
| 21 | II-4 | H$_3$CO—C$_6$H$_4$— | CN | bond | oil | 1.70(m, 2H), 1.80(m, 2H), 3.85(s, 3H), 7.0(dd, 2H), 8.1(dd, 2H) |
| 22 | II-5 | CF$_3$O—C$_6$H$_4$— | CN | bond | oil | 1.75(m, 2H), 1.87(m, 2H), 7.35(dd, 2H), 8.12(dd, 2H) |
| 23 | II-6 | CF$_3$—C$_6$H$_4$— | CN | bond | oil | 1.82(m, 2H), 1.93(m, 2H), 7.8(d, 2H), 8.15(d, 2H) |
| 24 | II-7 | 3-CF$_3$-4-Cl-C$_6$H$_3$— | CN | bond | amorphous | 1.9(m, 2H), 2.02(m, 2H), 7.55(d, 1H), 7.65(d, 2H), 7.76(s, 1H) |
| 25 | II-8 | C$_6$H$_5$—C$_6$H$_4$— | CN | bond | 118° C. | 1.75(m, 2H), 1.9(m, 2H), 7.45(m, 3H), 7.6(dd, 2H), 7.73(dd, 2H), 8.13(dd, 2H) |
| 26 | II-9 | 2-Cl-C$_6$H$_4$— | CN | bond | oil | 1.85(m, 2H), 1.95(m, 2H), 7.3–7.6(m, 4H) |
| 27 | II-10 | 3-F-4-Cl-C$_6$H$_3$— | CN | bond | | 1.8(m, 2H), 1.95(m, 2H), 7.25(m, 2H), 7.55(dd, 1H) |

TABLE 2-continued $$R^3-Y-\overset{\overset{O}{\|}}{C}-\underset{R^{2'}}{\triangleright}$$

| Ex. No. | Compd. No. | R³ | R²' | Y | Melting point (°C.) | Spectroscopic data, (¹H-NMR, CDCl₃, δ values in ppm) |
|---|---|---|---|---|---|---|
| 28 | II-11 | 2,3-difluorophenyl | CN | bond | | 1.85(m, 2H), 2.0(m, 2H), 7.03(dd, 2H), 7.5(m, 1H) |
| 29 | II-12 | 2,4-difluorophenyl | CN | bond | oil | 1.8(m, 2H), 1.95(m, 2H), 6.9-7.1(m, 2H), 7.65(m, 1H) |
| 30 | II-13 | 2,4-dichlorophenyl | CN | bond | | 1.85(m, 2H), 2.0(m, 2H), 7.4(s, 2H), 7.5(s, 1H) |
| 31 | II-14 | 2,4,5-trifluorophenyl | CN | bond | | 1.85(m, 2H), 1.96(m, 2H) 6.8(m, 2H) |
| 32 | II-16 | phenyl | CN | CH₂—CH₂ | | 1.6(m, 2H), 1.65(m, 2H), 2.95(t, 2H), 3.25(t, 2H) 7.2-7.4(m, 5H) |

EXAMPLE 33

2-(1-Cyanocyclopropyl)-2-(4-fluorophenyl)oxirane

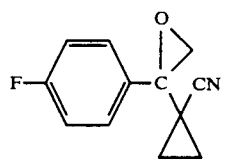

(IV-2)

130 ml of abs. DMSO are slowly added dropwise at 10° C. to 6.6 g (0.22 mol) of sodium hydride (80% in oil) and 34.2 g (0.16 mol) of trimethylsulphoxonium iodide. The mixture is stirred for one hour at 20° C. and then 26.3 g (0.14 mol) of 1-cyanocyclopropyl-4-fluorophenyl ketone (compound II-2, Example 19, dissolved in 65 ml of abs. DMSO) are added dropwise. The mixture is stirred for 14 h at 20° C. The solution is poured into water and the mixture is extracted with ethyl acetate. The combined organic phases are washed with H₂O and dried over Na₂SO₄, and the solvent is evaporated in vacuo. The residue is chromatographed on silica gel and 15 g (54% of theory) of 2-(1-cyanocyclopropyl)-2-(4-fluorophenyl)oxirane are obtained in the form of a colorless oil after evaporating the solvent, ¹H—NMR (CDCl₃):

δ=1.03-1.40 (m,4H), 2.95 (d,1H), 3.09 (d,1H), 7.07 (t,2H), 7.49 (dd,2H) ppm.

EXAMPLE 34

2-(1-Cyanocyclopropyl)-2-(2-phenylethyl)oxirane

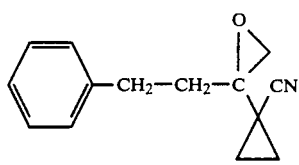

(IV-16)

10 ml of abs. DMSO are added dropwise at 10° C. to 2 g (10 mmol) of trimethylsulphonium iodide and 0.2 g (7 mmol) of sodium hydride (80% in oil). The mixture is stirred for 1 h at 20° C. After this, a solution of 1 g (5 mmol) of 1-cyanocyclopropyl 2-phenylethyl-ketone (compound II-16, Example 32) in 5 ml of abs. DMSO is added dropwise and the mixture is allowed to react for 4 h at 20° C. The solution is poured into water and extracted using ethyl acetate, the organic phase is dried with Na₂SO₄ and the solvent is evaporated in vacuo. 0.8 g (75% of theory) is obtained in the form of a colorless oil, $^1$H—NMR (CDCl$_3$):
δ=0.8–1.4 (m,4H), 2.03–3.20 (m, 1H) 2.24–2.42 (m,1H), 2.57–2.9 (m,4H) 7.14–7.33 (m, 5H) ppm.

TABLE 3

$$R^3-Y-\overset{O}{\triangle}-\triangle-R^{2'}$$

| Ex. No. | Compd. No. | R$^3$ | R$^{2'}$ | Y | Melting point (°C.) | Spectroscopic data ($^1$H-NMR, CDCl$_3$, δ values in ppm) |
|---|---|---|---|---|---|---|
| 35 | IV-1 | 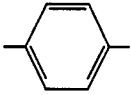 | CN | bond | oil | |
| 36 | IV-3 | 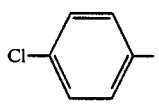 | CN | bond | oil | |
| 37 | IV-4 | 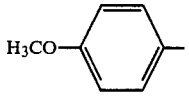 | CN | bond | oil | |
| 38 | IV-5 | 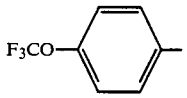 | CN | bond | oil | |
| 39 | IV-6 | 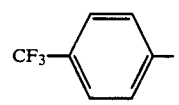 | CN | bond | oil | 0.9–1.40(m, 4H), 3.0(d, 1H), 3.1(d, 1H), 7.1–7.5(m, 4H) |
| 40 | IV-7 | 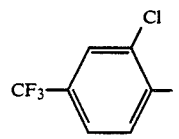 | CN | bond | oil | |
| 41 | IV-8 | 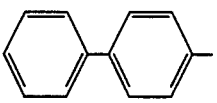 | CN | bond | oil | |
| 42 | IV-9 | 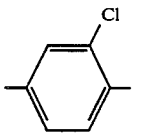 | CN | bond | oil | |
| 43 | IV-10 | 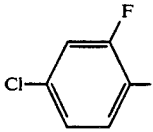 | CN | bond | oil | |
| 44 | IV-11 | 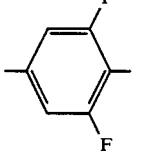 | CN | bond | oil | |

TABLE 3-continued $$R^3-Y-\underset{O}{\triangle}\underset{}{\triangle}-R^{2'}$$

| Ex. No. | Compd. No. | R³ | R²' | Y | Melting point (°C.) | Spectroscopic data (¹H-NMR, CDCl₃, δ values in ppm) |
|---|---|---|---|---|---|---|
| 45 | IV-12 | 2,4-difluorophenyl | CN | bond | oil | |
| 46 | IV-13 | 2,4-dichlorophenyl | CN | bond | oil | 0.9–1.3(m, 4H), 2.90(d, 1H), 3.26(d, 1H), 7.2–7.4(m, 3H) |
| 47 | IV-14 | 2,4,6-trifluorophenyl | CN | bond | oil | |
| 48 | IV-18 | 4-chlorophenyl | CN | CH₂—CH₂ | oil | |
| 49 | IV-19 | phenyl | CN | CH=CH | oil | |
| 50 | IV-20 | 4-chlorophenyl | CN | CH=CH | oil | |
| 51 | IV-21 | phenyl | CN | C≡C | oil | |

Use Examples

The substances indicated below were employed as comparison compounds in the following use examples: A, B (known form EP-OS 44,605) and C, D (known from EP-OS 180,850).

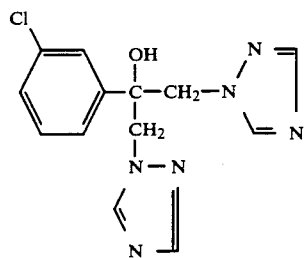

A

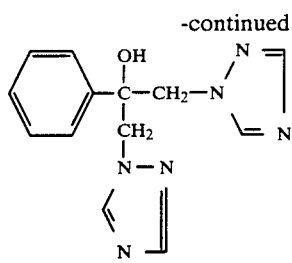

B

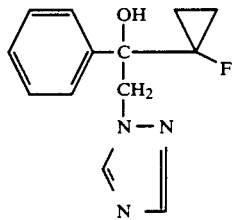

C

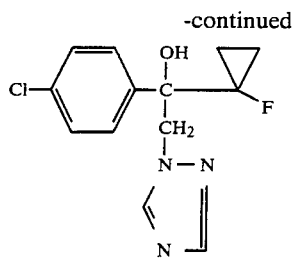

D

Example A

Antimycotic in vitro activity

Experimental description

The in vitro tests were carried out in a serial dilution test using inocula of microorganisms of on average $5 \times 10^4$ to $10^5$ microorganisms/ml of substrate. The nutrient medium used was a) for dermatophytes and Hyphomycetes
   Sabouraud's test medium
b) for yeasts
   meat extract-dextrose broth.

The incubation temperature was 28° C. to 37° C., and the incubation time was 24 to 96 hours with yeasts and 96 hours with dermatophytes and Hyphomycetes.

In this test, for example, the compounds according to the invention (I-3), (I-5), (I-14) and (I-16) show a better activity than the compounds (A) and (B) known from the prior art, in particular against Candida albicans.

Example B

Antimycotic in vivo activity (oral) in mouse candidosis

Experimental description:

Mice of the SPF-CF type were infected intravenously with $1-2 \times 10^6$ exponentially growing Candida cells which were suspended in physiological saline solution. One hour before and seven hours after the infection, the animals were treated orally in each case with 10–100 mg/kg of body weight of the preparation.

Result

Untreated animals died 3 to 6 days post infection. The survival rate on the 6th day post infection in untreated control animals was about 5%.

In this test, for example, the compounds according to the invention (I-2), (I-3), (I-4), (I-7), (I-9), (I-11), (I-13), (I-14), (I-15) and (I-16) show a good to very good action, i.e. >80% surviving on the 6th day p.i. and are thus better than the compounds (C) and (D) known from the prior art.

TABLE A

Antimycotic in vitro activity
MIC values in μg/ml of nutrient medium

| Active compound | Trichophyton mentagr. | Microsporum canis | Candida albicans | Torulopsis glabrata | Aspergillus fumigatus |
|---|---|---|---|---|---|
| (A) (known) | 32 | — | >64 | >64 | >64 |
| (B) (known) | 64 | — | 64 | >64 | >64 |
| Compounds according to Preparation Examples: | | | | | |
| I-3 | 2 | 4 | 2 | 8 | 4 |
| I-5 | <1 | 4 | 8 | 8 | 4 |
| I-14 | <1 | 4 | 2 | 16 | 4 |
| I-16 | <1 | <1 | 16 | 32 | 2 |

TABLE B

Antimycotic in vivo activity (oral) in mouse candidosis

| Active compound | Action |
|---|---|
| (C) (known) | n.a. |
| (D) (known) | n.a. |
| Compounds according to Preparation Example: | |
| I-2 | + + + + |
| I-3 | + + + + |
| I-4 | + + + + + |
| I-7 | + + + + + |
| I-9 | + + + + + |
| I-11 | + + + + + |
| I-13 | + + + |
| I-14 | + + + + + |
| I-15 | + + + + + |
| I-16 | + + + + |

Key:
+ + + + + = very good action = 90% surviving on the 6th day p.i.
+ + + + = good action = 80% surviving on the 6th day p.i.
+ + + = action = 60% surviving on the 6th day p.i.
+ + = weak action = 40% surviving on the 6th day p.i.
+ = trace action = under 40% surviving on the 6th day p.i.
n.a. = no difference to the untreated infection control

Example C

Antimicrobial in vivo activity (local) in the experimental guinea-pig trichophytosis model Experimental description White guinea-pigs of the Pirbright white strain were infected on the shaven, non-scarified back using a microconidia and macroconidia suspension of Trichophyton mentagrophytes.

The infected animals were treated locally from. The 3rd day 1x daily p.i. using a 2.5% strength solution of the preparation according to the invention (in dimethyl sulphoxide:glycerol = 1:4).

Result

In untreated animals, the typical picture of dermatophytosis with reddening, scaling and hair loss up to total integumental defect of the infection site developed in the course of 12 days p.i.

In this test, for example, the compounds according to the invention (I-2) and (I-3) show good action.

TABLE C

Antimycotic in vivo activity (local) in the experimental guinea-pig trichophytosis model

| Active compound Compound according to Preparation Example: | Action |
|---|---|
| (I-2) | + + + + |
| (I-3) | + + + + |

Explanation:
+ + + + + = very good action = no sign of infection on the 12th to 15th day p.i.
+ + + + = good action = slight reddening, isolated scaling
+ + + = action = reddening, scaling without hair loss
+ + = weak action = reddening, scaling, hair loss
+ = trace action = relatively extensive hair loss, inflammatory skin reaction

| Example D/Formulations | |
|---|---|
| 1. Solution: | |
| Active compound according to formula (I) | 10 g |
| Alcohol, pure (96% strength) | 300 g |
| Isopropyl myristate | 526 g |
| | 836 g |
| 2. Cream: | |
| Active compound according to formula (I) | 10 g |
| Aralcel 60 | 20 g |
| (sorbitan monostearate) | |
| Tween 60 | 15 g |
| (polyoxyethylene (2) sorbitan monostearate) | |
| Spermaceti, synthetic | 30 g |
| (mixture of esters of saturated $C_{14}$-$C_{18}$ fatty acids and $C_{14}$-$C_{18}$ fatty alcohols) | |
| Lanette O | 100 g |
| Eutanol G | 135 g |
| (2-octyldodecanol) | |
| Benzyl alcohol | 10 g |
| Water, demineralized | 680 g |
| | 1,000 g |

What is claimed is:

1. An azolylmethylcarbinol of the formula

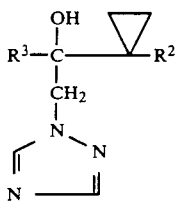

in which $R^2$ is cyano or the group

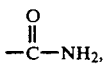

and $R^3$ is phenyl or phenyl which is substituted by identical or different substituents selected from the group consisting fluorine, chlorine, methoxy, trifluoromethyl, trifluoromethoxy and phenyl.

2. A compound according to claim 1, wherein such compound is 1-(1-cyanocyclopropyl)-1-(4-fluorophenyl)-2-(1,2,4-triazol-1-yl) ethanol of the formula

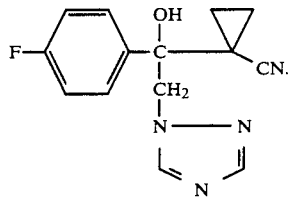

3. A compound according to claim 1, wherein such compound is 1-(1-cyanocyclopropyl)-1-(4-chlorophenyl)-2-(1,2,4-triazol-1-yl) ethanol of the formula

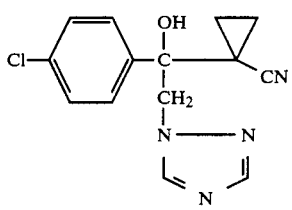

4. A compound according to claim 1, wherein such compound is 1-(1-cyanocyclopropyl)-1-(2,4-difluorophenyl)-2-(1,2,4-triazol-1-yl)ethanol of the formula

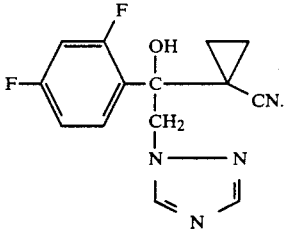

5. A compound according to claim 1, wherein such compound is 1-(1-cyanocyclopropyl)-1-(2,4-dichlorophenyl)-2-(1,2,4-triazol-1-yl)ethanol of the formula

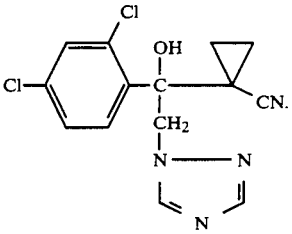

6. A pharmaceutical composition useful for combating mycoses comprising an azolymethylcarbinol according to claim 1 and a pharmaceutically acceptable excipient therefor.

7. A method of combating mycoses comprising administering to a patient in need of such treatment an effective amount of an azolymethylcarbinol according to claim 1.

8. A medicament in dosage unit form comprising an antimycotically effective amount of an azolylmethylcarbinol according to claim 1, either alone or in admixture with a suitable pharmaceutical excipient.

9. A method of combating mycoses in warm blooded animals comprising administering to said animal an antimycotically effective amount of an azolymethylcarbinol according to claim 1 either alone or in admixture with an inert excipient or in the form of a medicament.

* * * * *

UNITED STATES PATENT AND TRADEMARK OFFICE
CERTIFICATE OF CORRECTION

PATENT NO. : 5,059,615

DATED : October 22, 1991

INVENTOR(S) : Fugmann et al.

It is certified that error appears in the above-identified patent and that said Letters Patent is hereby corrected as shown below:

Col. 28, line 53    Delete " azolymethylcarbinol " and substitute
                    -- azolylmethylcarbinol --

Col. 28, line 58    Delete " azolymethylcarbinol " and substitute
                    -- azolylmethylcarbinol --

Col. 28, lines 65-66    Delete " azolymethylcarbinol " and substitute
                        -- azolylmethylcarbinol --

Signed and Sealed this

Twenty-eighth Day of September, 1993

*Attest:*

BRUCE LEHMAN

*Attesting Officer*    Commissioner of Patents and Trademarks